United States Patent [19]

Kising et al.

[11] Patent Number: 4,646,571
[45] Date of Patent: Mar. 3, 1987

[54] METHOD AND APPARATUS FOR HARDNESS MEASUREMENT

[75] Inventors: Jürgen Kising, Cologne; Stephan Bergerhausen, Erfstadt, both of Fed. Rep. of Germany

[73] Assignee: Krautkramer- Branson, Incorporated, Lewistown, Pa.

[21] Appl. No.: 769,337

[22] Filed: Aug. 26, 1985

[30] Foreign Application Priority Data

Feb. 11, 1985 [DE] Fed. Rep. of Germany ....... 3304535

[51] Int. Cl.$^4$ .......................... G01N 3/48; G01N 3/38; G01M 7/00
[52] U.S. Cl. ........................................ 73/573; 73/579
[58] Field of Search ............................. 73/573, 579, 81

[56] References Cited

U.S. PATENT DOCUMENTS

| | | | |
|---|---|---|---|
| 2,695,517 | 11/1954 | Wiggins | 73/573 |
| 3,153,338 | 10/1964 | Kleesattel | 73/573 |
| 3,572,097 | 3/1971 | Kleesattel | 73/573 |
| 3,955,404 | 5/1976 | Bickel et al. | 73/573 |
| 3,958,450 | 5/1976 | Kleesattel | 73/573 |
| 4,523,467 | 6/1985 | Diedericks et al. | 73/573 |

FOREIGN PATENT DOCUMENTS

| | | | |
|---|---|---|---|
| 2478426 | 9/1981 | France | 73/81 |
| 513308 | 5/1976 | U.S.S.R. | 73/573 |
| 550556 | 4/1977 | U.S.S.R. | 73/573 |

OTHER PUBLICATIONS

"Sensitivity of Hardness Measurement by the Acoustic Method"; *Sov. J. Nondest. Test.* (*USA*); vol. 17, No. 5 (May 1981); published Jan. 1982; V. A. Prikhod 'Ko et al; pp. 363-366.

"The Contact-Impedance Meter-2"; *Ultrasonics;* Oct. 1968; pp. 244-251; G. M. L. Gladwell et al.

*Primary Examiner*—Stewart J. Levy
*Assistant Examiner*—Tom Noland
*Attorney, Agent, or Firm*—Ervin B. Steinberg; Philip J. Feig

[57] ABSTRACT

This invention discloses a method and apparatus for determining the hardness of a solid workpiece. An elongated rod is excited to be mechanically resonant along its longitudinal axis and is provided at its front end with a defined contact surface of hard material (Vickers diamond). When the rod is rendered resonant at its natural frequency of vibration $\omega o$, the contact surface of the rod is pressed into the surface of the workpiece, whose hardness is to be determined, under a predetermined engagement force while the rod is forcibly maintained oscillating at the frequency $\omega o$. A sensor coupled to the rod provides a signal indicative of the amplitude of vibrations of the rod when in forced contact with the workpiece and such signal is fed to a computing device for providing a value indicative of the hardness of the workpiece.

4 Claims, 4 Drawing Figures

4,646,571

METHOD AND APPARATUS FOR HARDNESS MEASUREMENT

BRIEF SUMMARY OF THE INVENTION

The invention relates to a method for determining the hardness of solid bodies in which a rod rendered resonant and having a defined contact surface of hard material is applied with a predetermined contact force to a workpiece, the hardness of which is to be measured. The frequency of the mechanical vibrations causing the rod to be resonant is held constant and is equal to the resonant frequency ωo of the rod when it is not mechanically coupled to the workpiece.

As disclosed in U.S. Pat. No. 3,572,097 issued to C. Kleesattel dated Mar. 23, 1971, a vibrating rod is coupled to a workpiece and a characteristic parameter of this mechanically resonant device (e.g. the elasticity modulus or mechanical impedance) is varied until the frequency of vibration of the vibrating rod coupled to the workpiece is equal to ωo. The change in the characteristic parameter is then used to determine the hardness of the workpiece.

A disadvantage of this known method is that relatively complicated devices are necessary in order to vary the corresponding characteristic parameters and determine the correspondingly changed resonant frequency. U.S. Pat. No. 3,153,338 of C. Kleesattel dated Oct. 20, 1964; U.S. Pat. No. 3,955,404 of W. Bickel, et al. dated May 11, 1976, and U.S. Pat. No. 4,523,467 of R. Diederichs et al. dated June 18, 1985 disclose the measurement of hardness by using the difference between the resonant frequency of the probe when it is freely vibrating and when it is coupled to the workpiece. In the known devices, the hardness is usually measured in Vickers hardness values, i.e. the probe is provided with a diamond tip at its end. The softer the material of the workpiece, the greater is the area of indentation and the resulting change in resonant frequency.

The heretofore described method has been found disadvantageous in that the frequency measurement has to be relatively exact and the electronic circuits are complicated.

A principal object of this invention, therefore, is the provision of a method and apparatus making it unnecessary to cause a variation of the characteristic resonance parameters, or requiring a complicated measurement of frequency differences, without impairing the accuracy of measurement.

In contrast with the known methods, the present invention is not based on measuring the frequency difference of the vibrating rod, but is based on determining the amplitude of vibrations of the vibrating rod when the rod is mechanically coupled to the workpiece. This does not mean, as might at first sight be supposed, that the amplitude of oscillation is determined at the resonant frequency of the vibrating rod when it is coupled to the workpiece. Instead, the amplitude of vibrations of the rod is measured at the resonant frequency of the rod when it is oscillating free of such contact. It has been found, according to the invention, that the square of the amplitude of vibration is almost exactly proportional to the hardness of the workpiece.

Details and further advantages of this invention will be explained in more detail with reference to the following description when read in conjunction with the accompanying drawings.

DETAILED DESCRIPTION OF THE INVENTION

Figure 1:
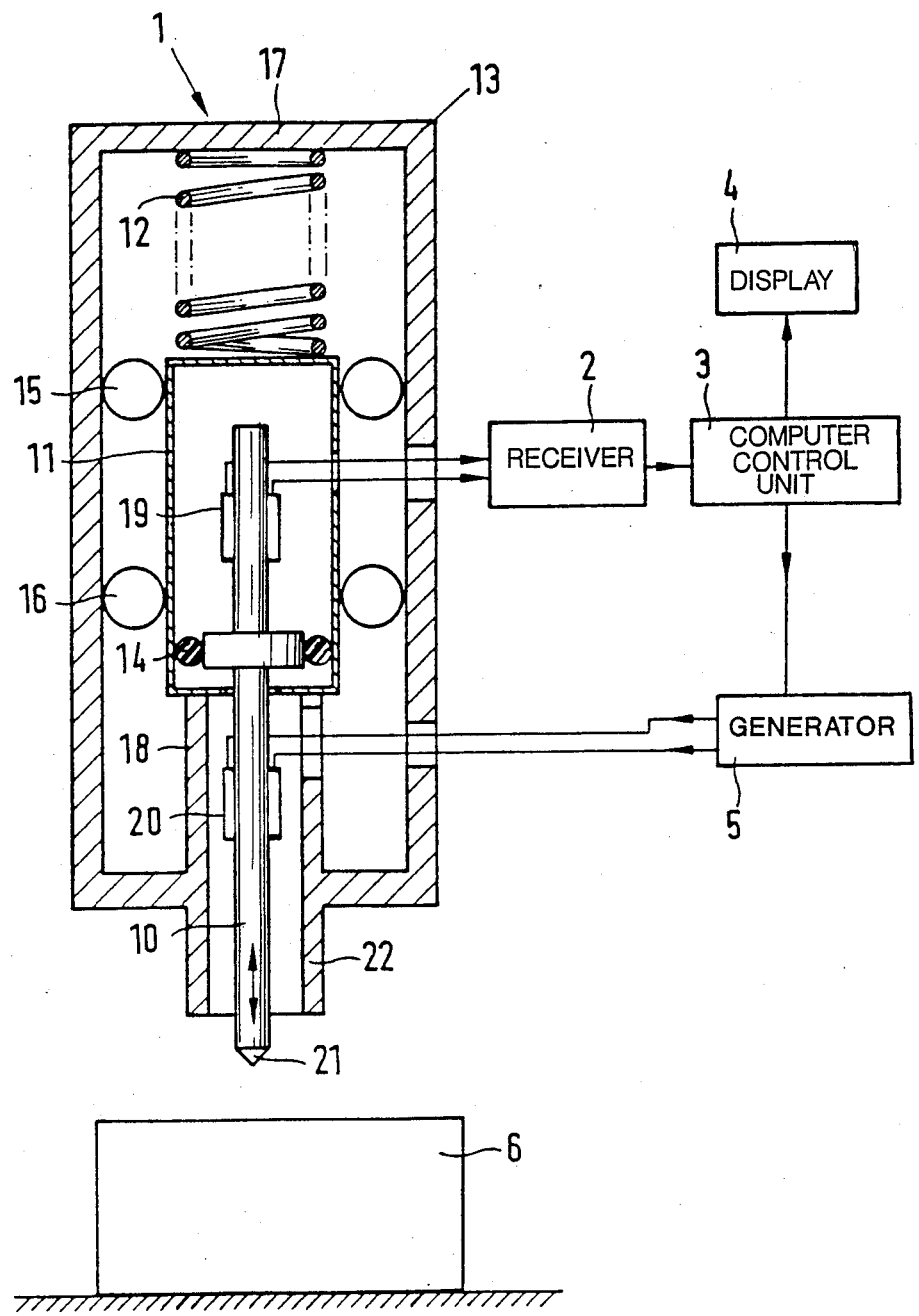
FIG. 1 is a schematic representation of the construction of the known hardness measuring instrument which can be used in the present invention.

Referring now to the figures, FIG. 1 shows the hardness probe 1 connected via a receiver 2 and a computer and control unit 3 to a measurement indicator 4. Probe 1 is also connected to a high frequency generator 5 which is actuated via the computer and control unit 3. Reference numeral 6 denotes the workpiece, the hardness of which is to be determined.

The probe 1 comprises in part a vibrating rod 10, a sleeve 11 partly surrounding the rod 10, a spring 12 and a casing 13 enclosing the aforementioned parts.

The rod 10 is resiliently held in the sleeve 11 by a hard rubber ring 14. Rod 10 and sleeve 11 can be fastened to the ring 14 by adhesive bonding. The lateral distance between sleeve 11 and casing 13 is determined by two spherical bushings 15 and 16. Along the longitudinal direction, the sleeve 11 is movable in the direction of the spring 12, starting from a predetermined distance relative to the top surface 17 of the casing 13. The predetermined distance is determined by a tubular inner cylinder 18 of casing 13, against which the sleeve 11 abuts when the rod 10 vibrates freely, i.e., free of contact with a workpiece, as seen in FIG. 1.

Two piezoelectric transducers 19 and 20 are secured to the rod 10. Transducer 19 serves as receiving transducer and is coupled to the receiver 2. Transducer 20 serves as a vibration exciting transducer and receives corresponding electrical high frequency signals from the high frequency generator 5. The bottom end of rod 10 bears a Vickers diamond 21, the indentation of which produced in the workpiece is to be determined indirectly. The diamond 21 provides a defined contact surface engaging the workpiece.

Probes of this kind are known and are used in conventional hardness gauges supplied by the assignee of this patent application under the name "Microdur". The main difference between the invention and the heretofore known devices is, firstly, the difference in the operation of the probe and, secondly, the electronic circuits coupled to the probe 1 which is not designed for determining frequency differences but for determining amplitudes of vibration.

In the prior art devices, as disclosed, for instance, in U.S. Pat. No. 3,153,338, which patent is incorporated herein by reference, the hardness is determined as follows:

The transducer 20 excites the rod 10 to cause it to vibrate along its longitudinal axis. The vibrations are sensed and received by the transducer 19 and sent via the receiver 2 and unit 3 (or another circuit device) to the high frequency generator 5. Generator 5 then varies the vibration frequency until it coincides with the natural frequency of the rod. This frequency $\omega o$ is then measured.

Figure 2:
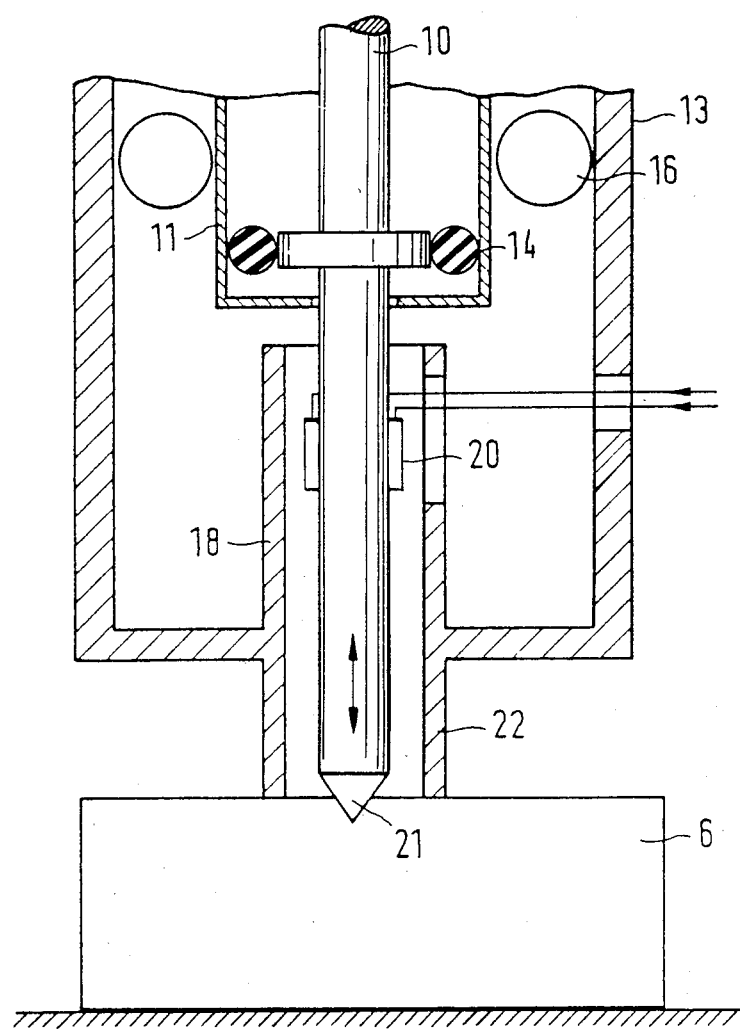
FIG. 2 shows a part of the instrument per FIG. 1, the vibrating rod being coupled to a workpiece.

Next, as shown in FIG. 2, rod 10 is pressed upon the workpiece 6 whose hardness is to be measured until the lower radial surface of cylinder 22 of casing 13 comes into contact with the workpiece 6. As a result, the diamond 21 penetrates into the surface of the workpiece 6 and the rod 10 no longer vibrates freely. The resonant frequency $\omega 1$ of the rod now coupled to the workpiece 6 is then redetermined using the previously described feedback circuit. The softer the material of the workpiece 6, the greater is the area of indentation and the resulting frequency shift $\Delta\omega = \omega 1 - \omega o$ is a measure of the hardness of the workpiece.

In the known hardness gauges, therefore, the frequency difference $\Delta\omega$ has to be determined very accurately and then converted in a relatively complicated manner to corresponding hardness values.

When using the method according to U.S. Pat. No. 3,572,097, the resonant frequency $\omega 1$ of the rod 10 when coupled to the workpiece 6 is varied until the value of $\Delta\omega$ is equal to zero. The resonant frequency is varied e.g. by means of an additional coil (not shown in FIG. 1) through which current flows and which is wound around the rod 10. The polarization current induced in the rod changes the elasticity modulus and thus changes the natural frequency of the rod. The polarization current at which the value $\Delta\omega$ is equal to zero is then used to determine the hardness.

By contrast, the device according to the present invention shown in FIG. 1 operates as follows:

Firstly, as before, the natural frequency of the freely vibrating rod 10 is determined as in the prior art. Next, the feedback signal between the receiver 2 and the high frequency generator 5 is interrupted, e.g. by the computer and control unit 3, so that the generator 5 produces only vibrations at the frequency $\omega o$. Next, as shown in FIG. 2, diamond 21 is pressed into the surface of workpiece 6 and the amplitude of vibration is measured at the frequency $\omega o$ by the receiver 2 and the corresponding hardness HV is determined in the computer and control unit 3.

It has been found that the relation between the measured amplitudes B and the hardness HV can be described fairly accurately as follows:

$$HV = C \cdot B^2 \cdot E_o^2 \quad (1)$$

wherein C is an instrument parameter and Eo is a modulus derived respectively from the modulus of elasticity E1 and E2 of the workpiece 6 and the diamond 21, and from the Poisson's ratios $\nu 1$ and $\nu 2$ of the workpiece and the diamond:

$$\frac{1}{E_o} = \frac{1}{E1/(1-\nu 1^2)} + \frac{1}{E2/(1-\nu 2^2)} \quad (2)$$

Advantageously the value of C is found by measuring the amplitude in a workpiece of known hardness, such as a calibration block, and solving the equation (1) with respect to value C. The Poisson's ratio $\nu 2$ and the modulus of elasticity E2 of the diamond are available from a table. The Poisson's ratio $\nu 1$ and the modulus of elasticity E1 of the workpiece are determined by measuring the longitudinal and transverse wave velocities (see "Ultrasonic Testing of Materials" by Krautkramer (book), 2nd edition, Springer Verlag, New York, N.Y., p. 580).

Figure 3:
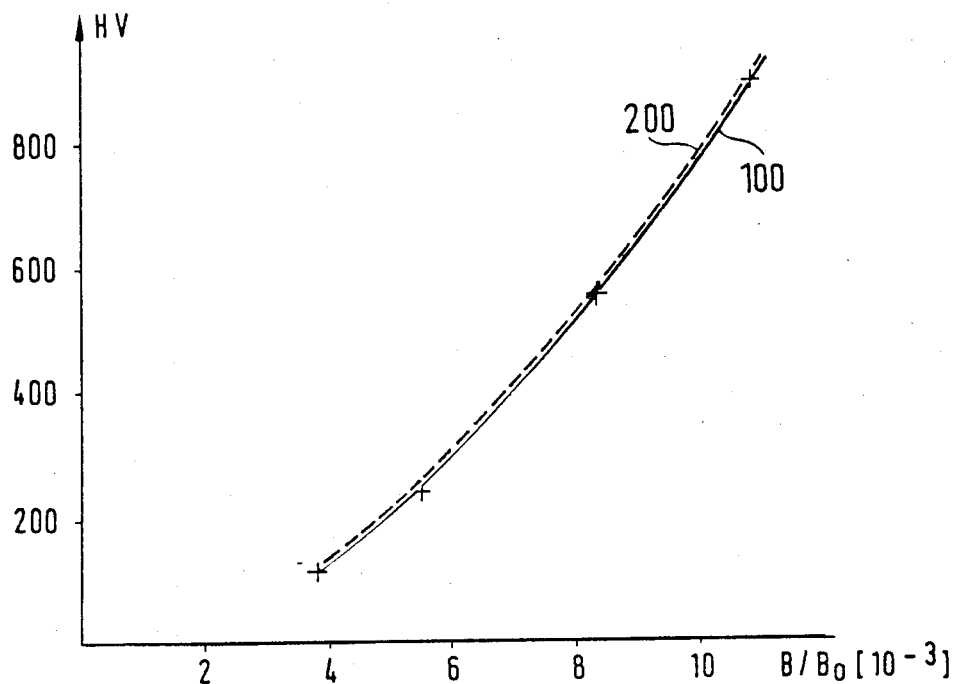
FIG. 3 is a graph showing the hardness measured on various workpieces and also calculated from the measured amplitudes.

FIG. 3 shows the measured hardness of various grades of steel. The relatively amplitude B/Bo is shown along the abscissa and the corresponding Vickers hardnesses (values HV) are plotted along the ordinate.

The value Bo denotes the voltage amplitude generated by the high frequency generator 5. In the embodiment, the value Bo was 20 V peak-to-peak for the freely-vibrating rod and the frequency value $\omega o$ was 78 kHz.

The force exerted by the spring 12 when the rod (FIG. 2) was placed on workpiece 6 was about 9.81N ($\triangleq$ 1 Kp). The corresponding indentation caused in the workpiece 6 by the diamond 21 was optically evaluated in a known manner, using a microhardness gauge, model 3212 made by Zwick GmbH & Co., Ulm, West Germany, the hardness being calculated from the diagonal of the base area of the permanent indentation. Curve 100 shows the optically measured hardness in dependence on the relative amplitude associated with the indentation.

The workpieces were four hardness comparison plates available to the inventors. Measurements with the aforementioned Zwick hardness gauge gave the following values: 120, 246, 563 and 879 HV 1/30.

The values of $E1/(1-\nu 1^2)$ for the hardness comparison plates used were: $2.34 \times 10^{11}$; $2.327 \times 10^{11}$; $2.269 \times 10^{11}$ and $2.233 \times 10^{11}$ Pa. The value obtained for $E2/(1-\nu 2^2)$ was $6 \times 10^{11}$ Pa. From these values, the value Eo was calculated, after which the corresponding hardness was calculated from the measured amplitudes and the constant C in equation (1). Curve 200 in FIG. 3 shows the result. The constant C was calculated using the hardness comparison plate having 563 HV 1/30.

$$\left( C = 7.27 \times 10^{-25} \frac{Kp}{(mm)^2 \, (mV)^2 \, (Pa)^2} \right)$$

As a comparison between curves 100 and 200 shows, the optically measured values and the values calculated from the amplitudes agree closely, practically through the entire range.

The following shall show that the relation found experimentally and defined by equation (1) can also be deduced by calculation:

When a cylindrical vibration rod free at both ends is excited by a periodic external force of frequency $\omega$, a standing wave is formed. The solution $u(x,t)$ of the wave equation for this case is:

$u(x,t) = [A(\omega) \times \sin(\omega t) + B(\omega) \times \cos(\omega t)] \cos(\kappa x)$ $\omega = 2\pi f$, $f$ = frequency of oscillation $\kappa = 2\pi/\lambda$, $\lambda$ = wavelength The expression in the square brackets represents the solution of the differential equation for a damped harmonic oscillator forced to vibrate at the frequency $\omega$. At every measuring point x, therefore, the rod behaves like a harmonic oscillator.

The quantities $A(\omega)$ and $B(\omega)$ depending on the excitation frequency are called the absorption amplitude and the dispersion amplitude respectively.

When the vibrating rod is in contact with a workpiece having a large mass, the following relation can be obtained from the articles by G. M. L. Gladwell and C. Kleesattel, "The Contact-Impedance Meter-2", Ultrasonics, October 1968, pages 244-251:

$$\Delta f = f_1 - f_0 \approx D \times E_o \times \sqrt{F}$$

wherein
fo=resonance frequency of freely-oscillating rod,
D=a constant depending only on the modulus of elasticity of the rod, the geometry of the rod and the indentation member, and
F=area of indentation by Vickers diamond.

This relation can be converted to:

$$\omega_1^2 = \omega_o^2 + D \times (\omega_1 + \omega_o) \times E_o \sqrt{F} \quad (3)$$

The absorption and the dispersion amplitudes, in the case of contact, have the following forms:

$$A(\omega) = B_o' \times (\Gamma \times \omega)/((\omega_1^2 - \omega^2)^2 + (\Gamma \times \omega)^2)$$

$$B(\omega) = B_o' \times (\omega_1^2 - \omega^2)/((\omega_1^2 - \omega^2)^2 + (\Gamma \times \omega)^2)$$

$\Gamma$=half-width of resonance frequency during contact, $B_o'$=amplitude of the periodic external force, which is proportional to the voltage amplitude $B_o$ of the high frequency generator 5.

If, during contact, the rod 10 is excited at the frequency $\omega = \omega_o = 2\pi f_o$, a simple relation for the dispersion amplitude $B(\omega)$ can be derived in view of the fact that the following conditions apply to steel in the hardness range $100 \leq HV \leq 1,000$ when in contact:

$$\Gamma < 200 \text{ Hz and } \Delta f > 300 \text{ Hz.}$$

In the present embodiment where $f_o$=78 kHz, therefore:

$$(\Gamma \omega_o)^2 << (\omega_1^2 - \omega^2)^2$$

and $$A(\omega) << B(\omega).$$

At the frequency $\omega = \omega_o$, the absorption amplitude $A(\omega)$ is already about two orders of magnitude smaller than the dispersion amplitude $B(\omega)$ and therefore negligible.

$B(\omega)$ can be simplified to:

$$B(\omega_o) \sim B_o'/(\omega_1^2 - \omega_o^2) \quad (4)$$

If one inserts equations (3) and (4) into the equation for the Vickers hardness:

$$HV = \text{test force/surface area of indentation} = K/F,$$

after solving equation (3) with respect to F, one obtains:

$$HV = C \times E_o^2 \times B(\omega_o)^2$$

with $C = K \times (D^2/B_o'^2) \times (\omega_1 + \omega_o)^2$.

Since $\Delta f/f_o < 2\%$ for the above-mentioned hardness range of steel, $(\omega_1 + \omega_o)^2$ and consequently C can be regarded as constant.

Figure 4:
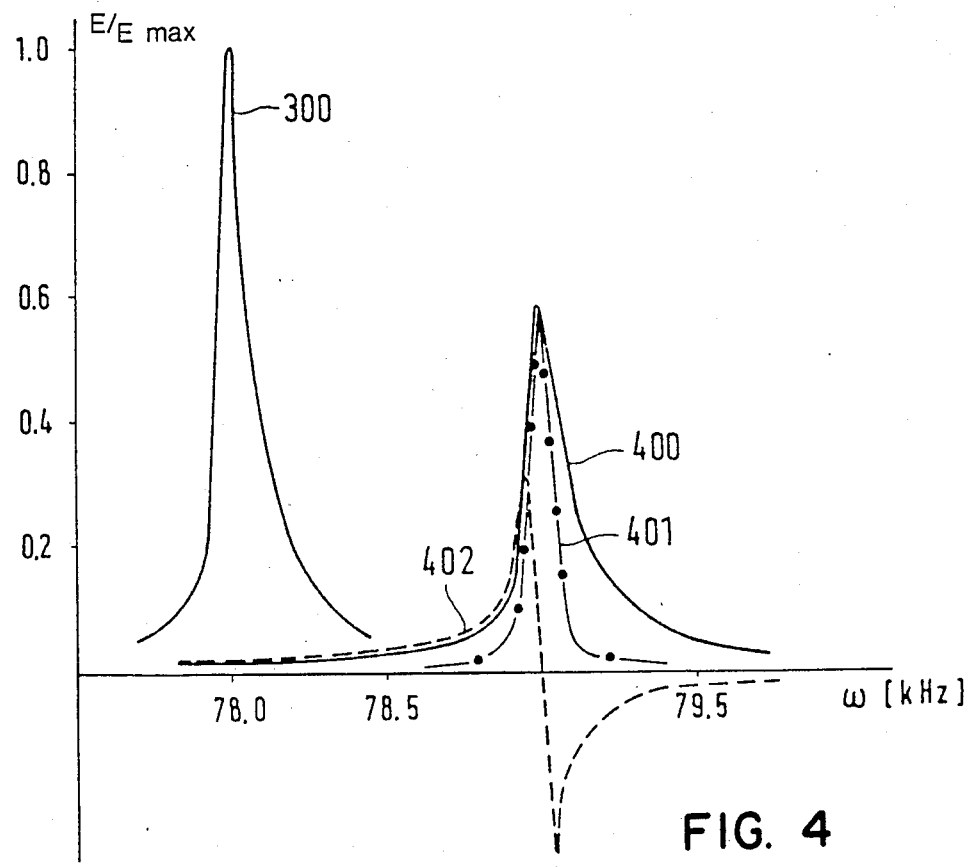
FIG. 4 is a graph for illustrating the invention.

In FIG. 4, the amplitudes measured are shown once more graphically for the present embodiment. The exciting frequency $\omega$ is plotted on the abscissa and the amplitudes sensed by the transducer 1 (FIG. 1) are plotted on the ordinate. The resonance curve marked 300 is obtained for the freely-vibrating rod 10 when $\omega$ varies. The corresponding resonant frequency $\omega_o$ is 78 kHz.

After the rod 10 makes contact with the workpiece 6 (see FIG. 1), resonance curve 300 becomes displaced. In the example shown in FIG. 4, the curve marked 400 is obtained when the vibrating rod is coupled to the workpiece. The corresponding resonant frequency $\omega_1$ in the illustrated example is 79 kHz. Numeral 401 denotes the calculated absorption curve $A(\omega)$ associated with the measured curve and numeral 402 denotes the corresponding dispersion curve calculated.

Since the actual frequency at which the rod 10 is energized is only 78 kHz when coupled to the workpiece, the receiver 2 (FIG. 1) receives only a relatively small voltage. In the example illustrated $E/E_{max} \approx 0.02$. The voltage calculated from this ratio substantially corresponds to the dispersion amplitude $B(\omega_o)$ because the corresponding proportion of the absorption amplitude is negligible at 78 kHz.

Basically, therefore, in the method according to the invention, the dispersion amplitude $B(\omega_o)$ of the vibrating rod is determined when coupled to the workpiece, and the resulting value is used as a measure of the hardness of the workpiece.

What is claimed is:

1. The method for determining the hardness of a solid workpiece comprising the steps:
   providing a rod having a defined contact surface;
   rendering said rod resonant along its longitudinal axis at its natural frequency $\omega_o$;
   bringing said defined contact surface into forced engagement with a workpiece the hardness of whichis to be measured with a predetermined engagement force while maintaining said rod vibratory at said frequency;
   providing a signal commensurate with the amplitude of vibrations of said rod when said rod is in said forced engagement with the workpiece and vibrating at said frequency $\omega_o$, and determining the hardness of the workpiece from said signal.

2. An apparatus for determining the hardness of a solid workpiece comprising:
   a rod having a defined contact end surface adapted to vibrate along its longitudinal axis;
   means coupled to said rod for rendering said rod resonant at its natural frequency;
   means for causing said defined contact end surface to be in contact with a workpiece, the hardness of which is to be determined, at a predetermined force while maintaining said rod vibrating at said frequency;
   means coupled to said rod for sensing the amplitude of vibration of said rod when said rod is in contact with the workpiece and vibrating at said frequency and providing a signal commensurate with such amplitude, and
   means for receiving said signal and determining the hardness of the workpiece therefrom.

3. An apparatus as set forth in claim 2, said means coupled to said rod for rendering said rod resonant including a high frequency generator providing an electrical signal to a first piezoelectric transducer means coupled to said rod; said means for sensing the amplitude of vibration of said rod including a second piezoelectric transducer means coupled to said rod, and said means for receiving said signal and determining the hardness including a computer means.

4. An apparatus as set forth in claim 3, said defined contact area end surface comprising a Vickers diamond, and said natural frequency being at a frequency in the ultrasonic frequency range.

* * * * *